(12) United States Patent
Watanabe et al.

(10) Patent No.: US 12,135,321 B2
(45) Date of Patent: Nov. 5, 2024

(54) OIL DETERIORATION DETECTION DEVICE, OIL DETERIORATION DETECTION SYSTEM, AND OIL DETERIORATION DETECTION METHOD

(71) Applicant: MITSUBISHI HEAVY INDUSTRIES, LTD., Tokyo (JP)

(72) Inventors: Ikumi Watanabe, Tokyo (JP); Toshiyasu Kiyabu, Tokyo (JP); Akihiko Yano, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 112 days.

(21) Appl. No.: 17/959,723

(22) Filed: Oct. 4, 2022

(65) Prior Publication Data

US 2023/0112726 A1    Apr. 13, 2023

(30) Foreign Application Priority Data

Oct. 13, 2021   (JP) ................................. 2021-168376

(51) Int. Cl.
*G01N 33/28*   (2006.01)
*G01N 27/02*   (2006.01)

(52) U.S. Cl.
CPC ......... *G01N 33/2888* (2013.01); *G01N 27/02* (2013.01)

(58) Field of Classification Search
CPC .............. G01N 33/28; G01N 33/2835; G01N 33/2847; G01N 33/2876; G01N 33/2888
See application file for complete search history.

(56) References Cited

U.S. PATENT DOCUMENTS

| 7,078,910 B2 * | 7/2006 | Hirthe | G01N 33/2888 |
| | | | 324/448 |
| 7,581,434 B1 * | 9/2009 | Discenzo | G01N 33/2888 |
| | | | 73/53.01 |
| 2002/0125899 A1 * | 9/2002 | Lvovich | G01N 27/026 |
| | | | 324/698 |
| 2003/0222656 A1 * | 12/2003 | Phillips | G01N 27/02 |
| | | | 324/605 |
| 2004/0085080 A1 | 5/2004 | Schilowitz et al. | |
| 2004/0239344 A1 * | 12/2004 | Hu | G01N 15/0656 |
| | | | 324/76.12 |

(Continued)

FOREIGN PATENT DOCUMENTS

| EP | 2533035 A1 * | 12/2012 | ........... D06F 39/004 |
| JP | 2005-529333 A | 9/2005 | |

(Continued)

*Primary Examiner* — Herbert K Roberts
(74) *Attorney, Agent, or Firm* — Birch, Stewart, Kolasch & Birch, LLP

(57) ABSTRACT

An oil deterioration detection device performs an analysis based on impedances at at least three first specific frequencies selected from a first frequency range to calculate an arc of impedance on a Nyquist diagram, the impedances being measured by applying an AC voltage at the at least three first specific frequencies to counter electrodes when oil to be evaluated passes between the counter electrodes, and when the calculated arc is larger than a reference arc calculated in advance of the oil to be evaluated by a predetermined value or larger, determines that moisture is mixed and calculates the amount of moisture based on the shape of the calculated arc.

10 Claims, 11 Drawing Sheets

(56) References Cited

U.S. PATENT DOCUMENTS

| | | | | |
|---|---|---|---|---|
| 2005/0021216 A1* | 1/2005 | Koehler | ............. | G01N 33/2888 |
| | | | | 701/108 |
| 2005/0110503 A1* | 5/2005 | Koehler | ............... | G01N 27/026 |
| | | | | 324/710 |
| 2008/0167823 A1* | 7/2008 | Koehler | ............... | G01N 27/026 |
| | | | | 702/65 |
| 2009/0315574 A1* | 12/2009 | Akiyama | ........... | G01N 33/2888 |
| | | | | 324/698 |
| 2017/0138876 A1* | 5/2017 | Potyrailo | .......... | G01N 33/2847 |
| 2017/0138922 A1* | 5/2017 | Potyrailo | ........... | G01N 33/2888 |
| 2019/0156600 A1* | 5/2019 | Potyrailo | ............. | G07C 5/0816 |
| 2020/0408844 A1* | 12/2020 | Ogasawara | ............ | G01K 13/00 |
| 2022/0326212 A1* | 10/2022 | Potyrailo | .............. | G01M 15/09 |

FOREIGN PATENT DOCUMENTS

| | | | |
|---|---|---|---|
| JP | 3729872 B2 | * | 12/2005 |
| JP | 2017-32352 A | | 2/2017 |

* cited by examiner

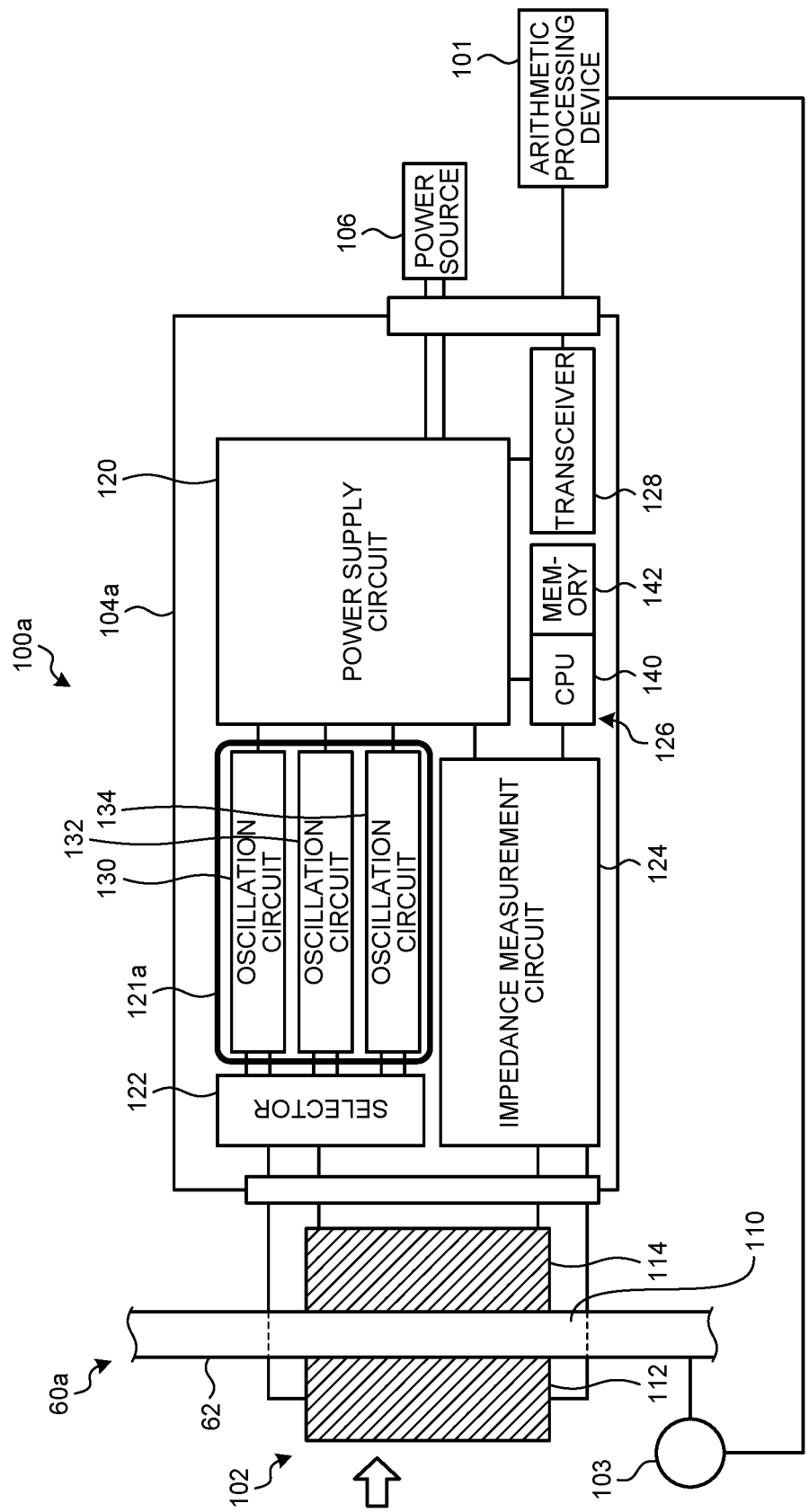

OIL DETERIORATION DETECTION DEVICE, OIL DETERIORATION DETECTION SYSTEM, AND OIL DETERIORATION DETECTION METHOD

CROSS-REFERENCE TO RELATED APPLICATIONS

The present application claims priority to and incorporates by reference the entire contents of Japanese Patent Application No. 2021-168376 filed in Japan on Oct. 13, 2021.

FIELD

The present disclosure relates to an oil deterioration detection device that detects deterioration of oil, an oil deterioration detection system, and an oil deterioration detection method.

BACKGROUND

Lubricating oil supplied to sliding parts, such as bearings, of devices deteriorates in performance as it is used. Patent Literature 1 describes a lubricating oil deterioration detection device as a device that detects deterioration of circulated oil. The lubricating oil deterioration detection device includes: a measuring unit that measures the permittivity of oil from the capacitance between electrodes disposed facing each other in a container; and a deterioration determining unit that performs a frequency analysis on the results of measurement by the measuring unit and determines whether the deterioration state of lubricating oil is in a predetermined acceptable state.

Patent Literature 2 describes a method for checking the state of working fluid. The method includes: disposing a pair of separated electrodes in a fluid; supplying an AC signal to the electrodes over four or more frequency ranges; measuring impedance or admittance data as a function of the frequency from an electrical response to the supplied AC signal, measuring at least one item selected from a group composed of resistance, capacitance, maximum value of omega, impedance, and time constant; and comparing the measured property with a predetermined value of the property and measuring an index of the state of the fluid.

CITATION LIST

Patent Literature

Patent Literature 1: Japanese Patent Application Laid-open No. 2017-32352
Patent Literature 2: Japanese Translation of PCT International Application Publication No. 2005-529333

SUMMARY

Technical Problem

Oil performance can be evaluated by various criteria as described in Patent Literatures 1 and 2. The detection methods described in Patent Literatures 1 and 2, however, may possibly fail to evaluate deterioration of oil depending on the cause of deterioration of oil.

In view of the disadvantage described above, an object of the present disclosure is to provide an oil deterioration detection device, an oil deterioration detection system, and an oil deterioration detection method that can detect deterioration of oil more precisely.

Solution to Problem

To achieve the object, an oil deterioration detection device according to the present disclosure is configured to: perform an analysis based on impedances at at least three first specific frequencies selected from a first frequency range to calculate an arc of impedance on a Nyquist diagram, the impedances being measured by applying an AC voltage at the at least three first specific frequencies to counter electrodes when oil to be evaluated passes between the counter electrodes, and when the calculated arc is larger than a reference arc calculated in advance of the oil to be evaluated by a predetermined value or larger, determine that moisture is mixed and calculate an amount of moisture based on a shape of the calculated arc.

To achieve the object, an oil deterioration detection method according to the present disclosure includes: measuring impedances by applying an AC voltage at at least three first specific frequencies selected from a first frequency range to counter electrodes when oil to be evaluated passes between the counter electrodes; performing an analysis based on the measured impedances at the at least three first specific frequencies to calculate an arc of impedance on a Nyquist diagram; and when the calculated arc is larger than a reference arc calculated in advance of the oil to be evaluated by a predetermined value or larger, determining that moisture is mixed and calculating an amount of moisture based on the shape of the calculated arc.

Advantageous Effects of Invention

The present disclosure can detect deterioration of oil more precisely.

BRIEF DESCRIPTION OF DRAWINGS

FIG. 16 is a schematic of a schematic configuration of the oil deterioration detection system according to the present embodiment.

DESCRIPTION OF EMBODIMENTS

Exemplary embodiments according to the present disclosure are described below in greater detail with reference to the accompanying drawings. The embodiments are not intended to limit the present disclosure. If there are a plurality of embodiments, an embodiment obtained by combining the embodiments is included in the scope of the present disclosure.

Figure 1:
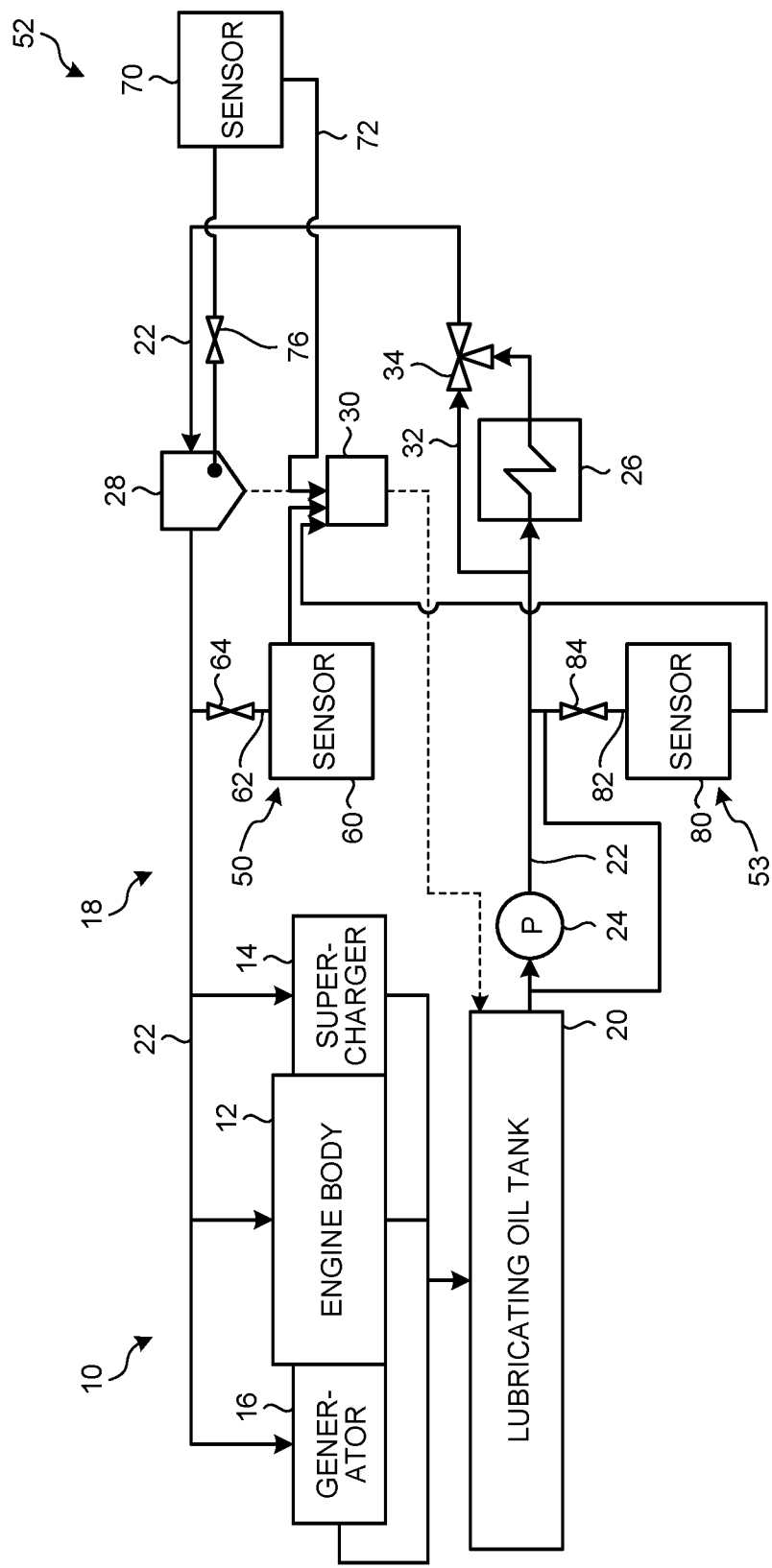
FIG. 1 is a block diagram of a schematic configuration of a power generation unit including an oil deterioration detection system according to the present embodiment.

FIG. 1 is a block diagram of a schematic configuration of a power generation unit including an oil deterioration detection system according to the present embodiment. While the oil deterioration detection system according to the present embodiment is used to measure deterioration (state) of lubricating oil in the power generation unit, the use of the oil deterioration detection system is not limited thereto. The oil deterioration detection system can be used to detect the state (deterioration state) of various lubricating oils and working oils.

A power generation unit 10 according to the present embodiment includes an engine body 12, a supercharger 14, a generator 16, and a lubricating oil supply unit 18. The engine body 12 is an engine, such as a gas or diesel engine, and burns fuel to rotate a rotating shaft. The supercharger 14 is a compressor that rotates integrally with a turbine rotated by energy discharged from the engine body 12. The supercharger 14 compresses and supplies air to the engine body 12. The generator 16 is coupled to the engine body 12 and is rotated by the engine body 12, thereby generating electricity.

The lubricating oil supply unit 18 supplies lubricating oil to the engine body 12, the supercharger 14, and the generator 16 and collects lubricating oil discharged from the engine body 12, the supercharger 14, and the generator 16. The lubricating oil supply unit 18 includes a lubricating oil tank 20, a lubricating oil line 22, a pump 24, a cooler 26, a filter 28, a backwash strainer 30, bypass piping 32, a three-way valve 34, a first sensor unit 50, a second sensor unit 52, and a third sensor unit 54. While the present embodiment includes three sensor units to indicate their arrangement positions, deterioration of lubricating oil can be detected by one sensor unit.

The lubricating oil tank 20 stores therein lubricating oil discharged from the engine body 12, the supercharger 14, and the generator 16. The lubricating oil line 22 connects the lubricating oil tank 20 to the engine body 12, the supercharger 14, and the generator 16. The lubricating oil line 22 supplies oil in the lubricating oil tank 20 to the engine body 12, the supercharger 14, and the generator 16 and discharges lubricating oil in the engine body 12, the supercharger 14, and the generator 16 to the lubricating oil tank 20. The pump 24 is disposed in the lubricating oil line 22 and supplies lubricating oil in the lubricating oil tank 20 to the engine body 12, the supercharger 14, and the generator 16. The lubricating oil supply unit 18 cools the lubricating oil by the cooler 26, removes foreign matter by the filter 28, and sends the lubricating oil by the pump 24, thereby supplying the lubricating oil to the engine body 12, the supercharger 14, and the generator 16.

The cooler 26 is disposed on the downstream of the pump 24 in the lubricating oil line 22. The cooler 26 cools lubricating oil flowing through the lubricating oil line 22. The filter (main strainer) 28 is disposed on the downstream of the cooler 26 in the lubricating oil line 22. The filter 28 removes foreign matter included in the lubricating oil flowing through the lubricating oil line 22. The lubricating oil that has passed through the filter 28 is supplied to the engine body 12, the supercharger 14, and the generator 16. The filter 28 removes the removed foreign matter by backwashing. The backwash strainer 30 is supplied with lubricating oil discharged in the backwashing of the filter 28. The backwash strainer 30 removes foreign matter from the lubricating oil discharged in the backwashing of the filter 28 and discharges the lubricating oil from which the foreign matter is removed to the lubricating oil tank 20.

The bypass piping 32 is piping that bypasses the cooler 26. The three-way valve 34 connects a line passing through the cooler 26, the bypass piping 32, and the filter 28. The three-way valve 34 switches between the state where the line passing through the cooler 26 is connected to the filter 28 and the state where the bypass piping 32 is connected to the filter 28. Thus, the three-way valve 34 determines whether to cause the lubricating oil to pass through the cooler 26, thereby controlling the temperature of the lubricating oil. In addition, the three-way valve 34 connects both the line passing through the cooler 26 and the bypass piping 32 to the filter 28 and adjusts the degrees of opening. Thus, the three-way valve 34 can adjust the ratio between the flow rate of the lubricating oil passing through the cooler 26 and the flow rate of the lubricating oil passing through the bypass piping 32. The three-way valve 34 adjusts the ratio between the flow rate of the lubricating oil passing through the cooler 26 and the flow rate of the lubricating oil passing through the bypass piping 32, thereby controlling the temperature of the lubricating oil.

The first sensor unit 50 detects the deterioration state of the lubricating oil flowing through the lubricating oil line 22. The first sensor unit 50 includes an oil deterioration detection system 60, a sensor line 62, and a valve 64. The oil deterioration detection system 60 detects the deterioration state of the lubricating oil. The oil deterioration detection system 60 will be described later. One end of the sensor line 62 is connected to a position on the downstream of the filter 28 in the lubricating oil line 22, and the other end is connected to the backwash strainer 30. Part of the lubricating oil that has passed through the filter 28 flows into the sensor line 62, passes through the oil deterioration detection system 60, and is discharged to the backwash strainer 30. The valve 64 is disposed in the sensor line 62 and switches between opening and closing to determine whether to supply the lubricating oil to the oil deterioration detection system 60. The valve 64 also functions as a flow rate control valve that controls the flow rate of the lubricating oil supplied to the oil deterioration detection system 60 by adjusting the degree of opening.

The second sensor unit 52 detects the deterioration state of the lubricating oil flowing through the lubricating oil line 22. The second sensor unit 52 includes an oil deterioration detection system 70, a sensor line 72, and a valve 76. The oil deterioration detection system 70 detects the deterioration state of the lubricating oil similarly to the oil deterioration detection system 60. One end of the sensor line 72 is connected to the filter 28, and the other end is connected to the backwash strainer 30. The lubricant oil in the filter 28 flows into the sensor line 72, passes through the oil deterioration detection system 70, and is discharged to the backwash strainer 30. The valve 76 is disposed in the sensor line 72 and switches between opening and closing to determine whether to supply the lubricating oil to the oil deterioration detection system 70. The valve 76 also functions as a flow rate control valve that controls the flow rate of the lubricating oil supplied to the oil deterioration detection system 70 by adjusting the degree of opening.

The third sensor unit 54 detects the deterioration state of the lubricating oil flowing through the lubricating oil line 22. The third sensor unit 54 includes an oil deterioration detection system 80, a sensor line 82, and a valve 84. The oil deterioration detection system 80 detects the deterioration state of the lubricating oil. The oil deterioration detection system 80 will be described later. One end of the sensor line 82 is connected to a position between the lubricating oil tank 20 and the pump 24 in the lubricating oil line 22, and the other end is connected to the backwash strainer 30. Part of the lubricating oil stored in the lubricating oil tank 20 flows into the sensor line 82, passes through the oil deterioration detection system 80, and is discharged to the backwash strainer 30. The valve 84 is disposed in the sensor line 82 and switches between opening and closing to determine whether to supply the lubricating oil to the oil deterioration detection system 80. The valve 84 also functions as a flow rate control valve that controls the flow rate of the lubricating oil supplied to the oil deterioration detection system 80 by adjusting the degree of opening.

The first sensor unit 50, the second sensor unit 52, and the third sensor unit 54 allow the lubricating oil to pass therethrough from the filter 28 to the backwash strainer 30 due to the difference in pressure of the lubricating oil and can supply the lubricating oil to the oil deterioration detection system 60 without any driving force, such as a pump. While the present embodiment includes the first sensor unit 50, the second sensor unit 52, and the third sensor unit 54, the deterioration state of the lubricating oil can be measured by any one of the sensor units as described above. The arrangement positions of the sensor units are not limited thereto.

The oil deterioration detection systems 60, 70, and 80 are described below with reference to FIG. 2. The following describes the oil deterioration detection system 60 as a representative system because the oil deterioration detection systems 60, 70, and 80 have the same basic configuration except for the arrangement positions.

Figure 2:
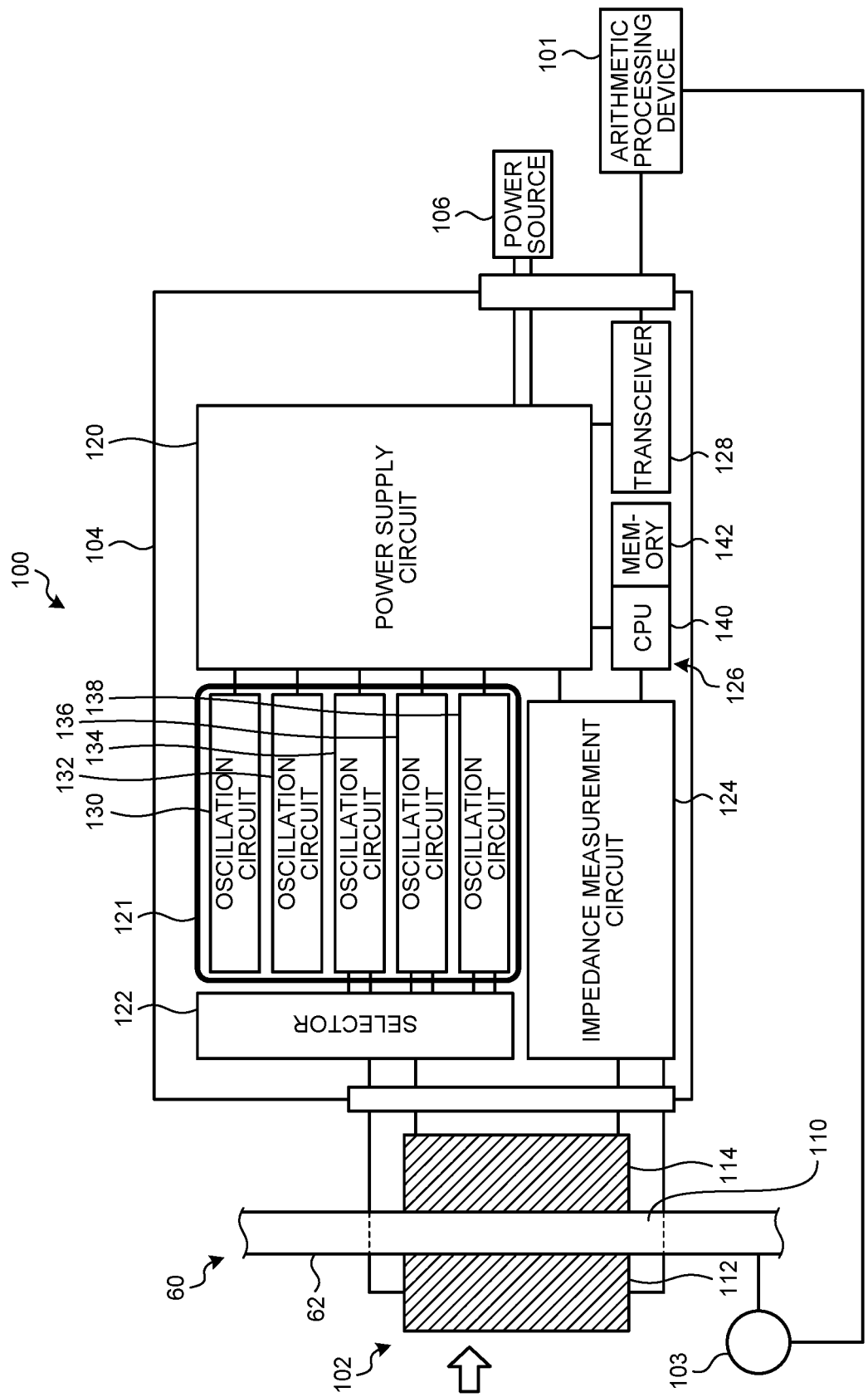
FIG. 2 is a schematic of a schematic configuration of the oil deterioration detection system according to the present embodiment.

FIG. 2 is a schematic of a schematic configuration of the oil deterioration detection system according to the present embodiment. The oil deterioration detection system 60 measures the deterioration state of the lubricating oil flowing into the sensor line 62. The oil deterioration detection system 60 includes a measurement device 100, an arithmetic processing device (oil deterioration detection device) 101, and a temperature detecting unit 103. In the oil deterioration detection system 60 according to the present embodiment, the measurement device 100, the temperature detecting unit 103, and the arithmetic processing device (oil deterioration detection device) 101 are closely disposed and connected by wiring and transmit and receive data via the wiring. The present embodiment is not limited thereto. The arithmetic processing device (oil deterioration detection device) 101 may wirelessly communicate with the measurement device 100 and the temperature detecting unit 103. Alternatively, the arithmetic processing device (oil deterioration detection device) 101 may transmit and receive data to and from the measurement device 100 and the temperature detecting unit 103 via a public communication network.

The measurement device 100 applies an AC voltage to the lubricating oil flowing through the sensor line 62 and detects fluctuations in impedance of the lubricating oil to the AC voltage. The measurement device 100 can switch the frequency of the AC voltage between a plurality of values and detects the impedance of the lubricating oil to the AC voltage of a plurality of frequencies.

The measurement device 100 includes a measuring unit 102, a substrate 104, and a power source 106. The power source 106 supplies electric power to the substrate 104. The measuring unit 102 includes a flow path 110, a counter electrode 112, and an action electrode 114. The flow path 110 is a path connected to the sensor line 62 and through which hydraulic oil flowing through the sensor line 62 flows. The counter electrode 112 and the action electrode 114 are two flat electrodes facing each other with the flow path 110 interposed therebetween. The counter electrode 112 and the action electrode 114 serve as part of the wall surface of the flow path 110. In other words, the counter electrode 112 and the action electrode 114 are in contact with the hydraulic oil flowing through the flow path 110.

The substrate 104 generates an AC voltage to be applied to the counter electrode 112 and the action electrode 114 of the measuring unit 102 and supplies it to the counter electrode 112 and the action electrode 114 to measure the impedance of the lubricating oil to which the AC voltage is applied. The substrate 104 includes a power supply circuit 120, a frequency control unit 121, a selector 122, an impedance measurement circuit 124, an arithmetic unit 126, and a communication unit 128.

The power supply circuit 120 is connected to the power source 106 and supplies electric power supplied from the power source 106 to each unit, specifically to the frequency control unit 121, the impedance measurement circuit 124, the arithmetic unit 126, and the communication unit 128. The power supply circuit 120 raises and lowers the voltage of the electric power supplied from the power source 106 and supplies it to each unit at necessary current and voltage. The power supply circuit 120 may also have a function to convert an alternating current into a direct current or a function to convert a direct current into an alternating current.

The frequency control unit 121 converts the frequency of the voltage supplied from the power supply circuit. The frequency control unit 121 includes oscillation circuits 130, 132, 134, 136, and 138. The oscillation circuits 130, 132, 134, 136, and 138 generate AC voltages at different set frequencies. The oscillation circuits 130, 132, and 134 generate AC voltages at first specific frequencies selected from a first frequency range. The oscillation circuits 136 and 138 generate AC voltages at second specific frequencies selected from a second frequency range.

The first frequency range is a range of frequencies processed by the arithmetic processing device 101 to determine the amount of moisture and the base number of the lubricating oil. The first frequency range is preferably 50 mHz to 7 MHz. One of the first specific frequencies is 50 mHz to 10 Hz, one of the first specific frequencies is 10 Hz to 500 Hz, and one of the first specific frequencies is 500 Hz to 7 MHz. For example, the oscillation circuit 130 generates an AC voltage at a specific frequency of 1 kHz, the oscillation circuit 130 generates an AC voltage at a specific frequency of 100 Hz, and the oscillation circuit 130 generates an AC voltage at a specific frequency of 1 Hz.

The second frequency range is a range of frequencies processed by the arithmetic processing device 101 to determine soot included in the lubricating oil and is a range of lower frequencies than the first frequency range. The second frequency range is preferably 0.25 mHz to 50 mHz. One of the second specific frequencies is 10 mHz to 50 mHz, and one of the second specific frequencies is 0.25 mHz to 10 mHz. For example, the oscillation circuit 136 generates an AC voltage at a specific frequency of 8 mHz, and the oscillation circuit 138 generates an AC voltage at a specific frequency of 1 mHz. The first specific frequencies and the second specific frequencies are given by way of example only and are not limited thereto.

The selector 122 is disposed between the frequency control unit 121 and the counter electrode 112 and the action electrode 114. The selector 122 selects one oscillation circuit from the oscillation circuits 130, 132, 134, 136, and 138 and applies the AC voltage generated by the selected circuit to the counter electrode 112 and the action electrode 114.

The impedance measurement circuit 124 detects the timing of applying the AC voltage and the amplitude of the current value from the counter electrode 112 and the action electrode 114 to which the AC voltage is applied, thereby measuring the impedance of the lubricating oil flowing through the flow path 110. The impedance measurement circuit 124 transmits the detected impedance value to the arithmetic processing device 101.

The arithmetic unit 126 generates signals that cause the substrate 104 to perform various kinds of processing. The arithmetic unit 126 includes a CPU 140 and a memory 142. The CPU (central processing unit) 140 performs various arithmetic operations. The memory 142 serves as a working area for arithmetic processing performed by the CPU 140 and stores therein the results of arithmetic operations of the CPU 140. The memory 142 also stores therein computer programs for the arithmetic processing performed by the CPU 140. The communication unit 128 communicates with the arithmetic processing device 101 and outputs the results of measurement of the impedance.

The arithmetic processing device 101 analyzes the results of measurement by the measurement device 100, converts the impedance of the lubricating oil into an RC equivalent circuit, and creates a Nyquist diagram based on the converted results. The arithmetic processing device 101 has information on the characteristics on the Nyquist diagram serving as the reference of the lubricating oil. The arithmetic processing device 101 compares the analysis results with the reference value and calculates the deterioration state of the lubricating oil, that is, the moisture value, the base number, and the amount of soot based on the results of comparison. The analysis method will be described later. The arithmetic processing device 101 is what is called a personal computer, a tablet, or the like and includes an arithmetic unit, such as a CPU, a storage device, such as a ROM and a RAM, an input unit with which an operator performs operations, and a display unit, for example. Besides the computer programs for performing arithmetic processing, the arithmetic processing device 101 calculates in advance and stores therein information on parameters serving as criteria for evaluation, results of an analysis of the lubricating oil serving as the reference, criteria for calculating the moisture value, the base number, and the amount of soot based on deviation from the reference value, and information on fluctuation values due to temperature, for example.

The temperature detecting unit 103 detects the temperature of the lubricating oil flowing through the sensor line 62. The temperature detecting unit 103 transmits the detection results to the arithmetic processing device 101.

Figure 3:
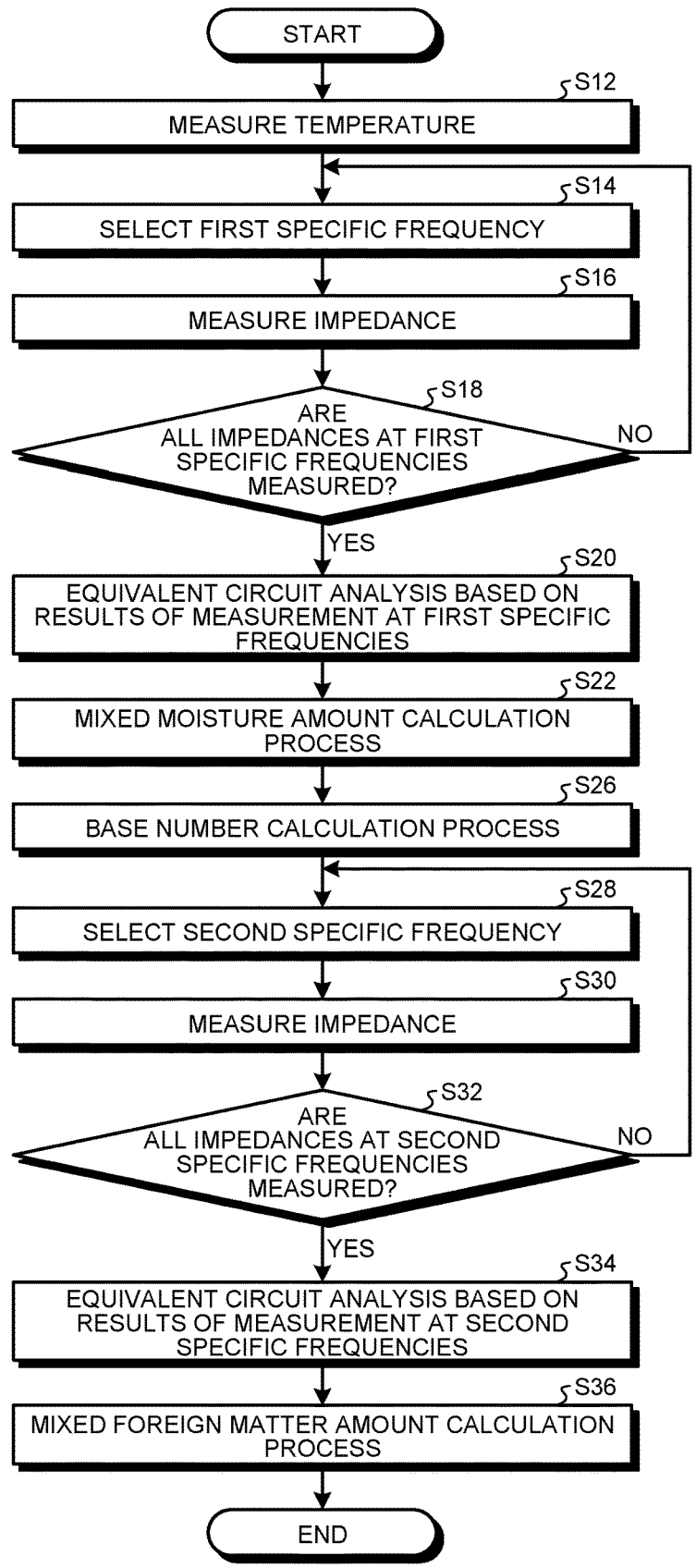
FIG. 3 is a flowchart of an example of an oil deterioration detection method performed by the oil deterioration detection system according to the present embodiment.
Figure 4:
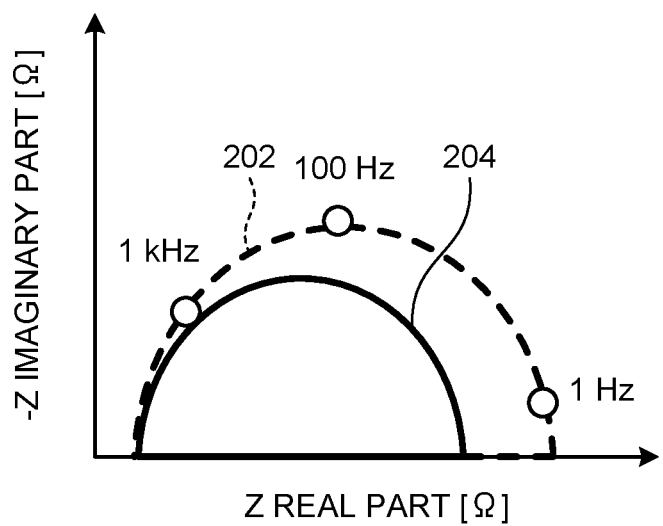
FIG. 4 is a diagram for explaining the oil deterioration detection method.
Figure 5:
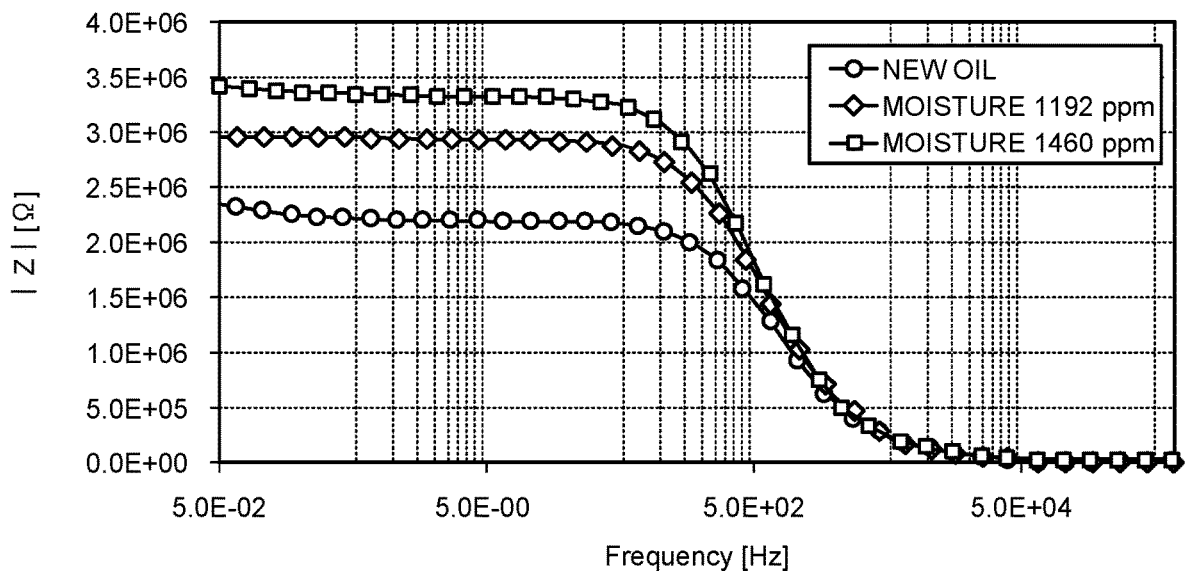
FIG. 5 is a diagram for explaining a process of detecting the amount of moisture.
Figure 6:
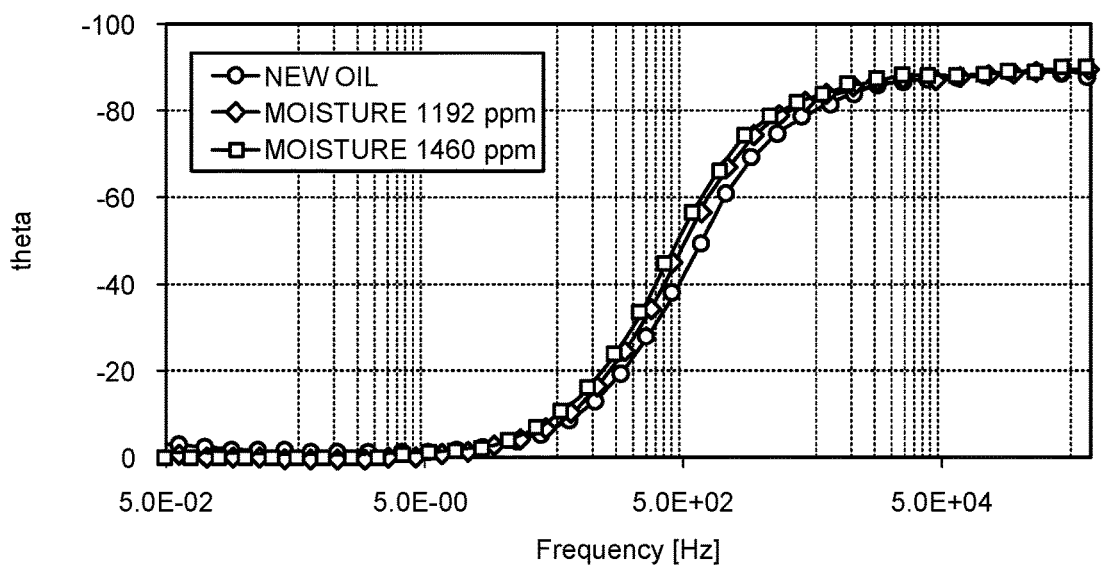
FIG. 6 is a diagram for explaining the process of detecting the amount of moisture.
Figure 7:
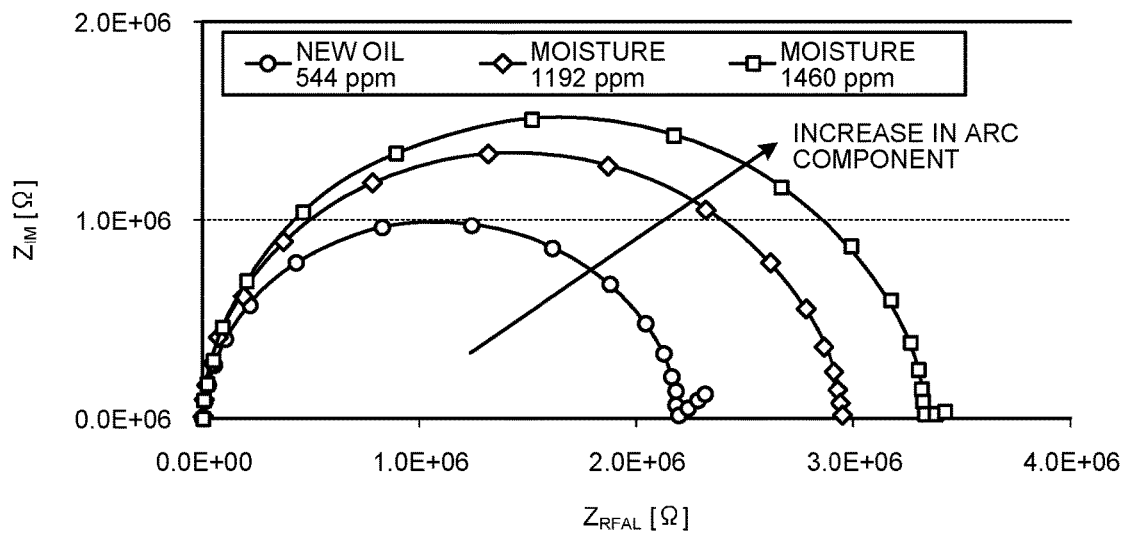
FIG. 7 is a diagram for explaining the process of detecting the amount of moisture.
Figure 8:
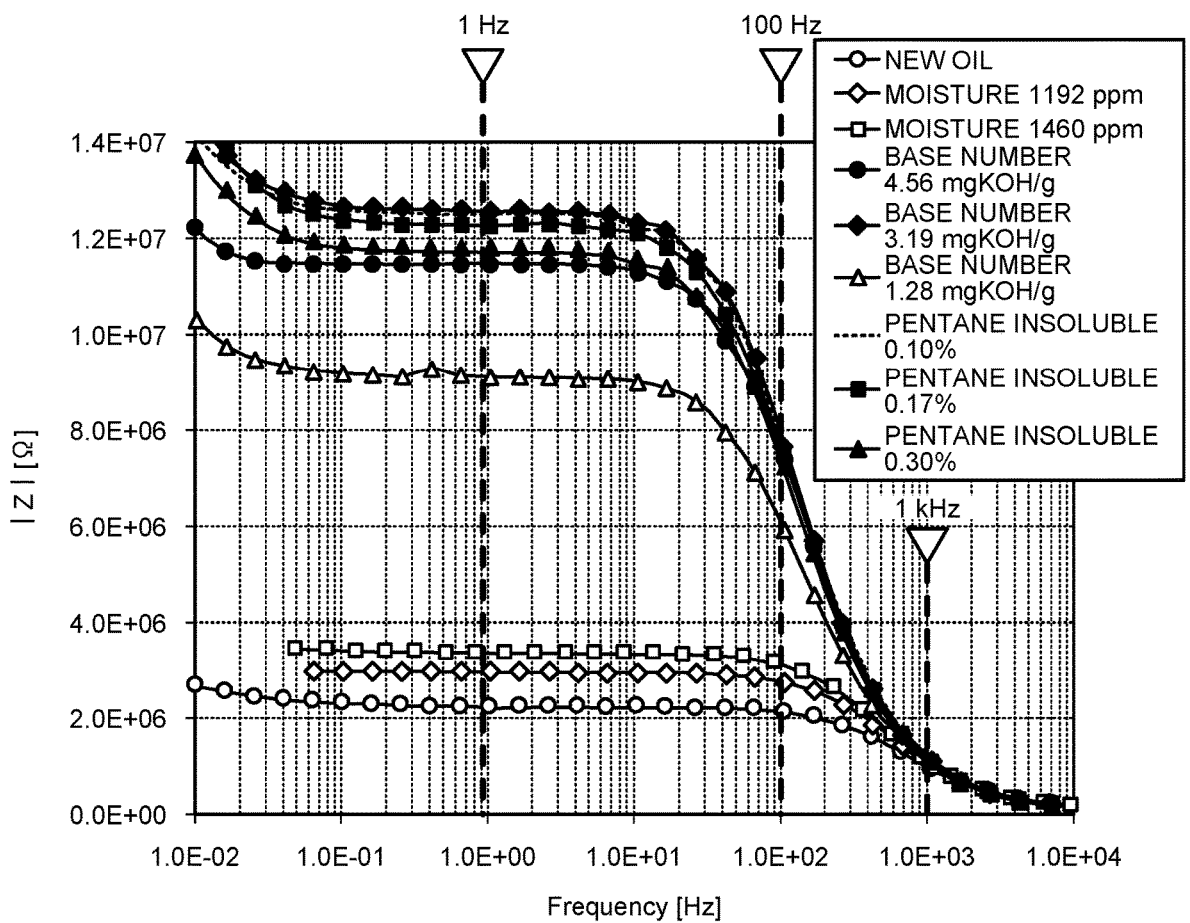
FIG. 8 is a diagram for explaining the oil deterioration detection method.
Figure 9:
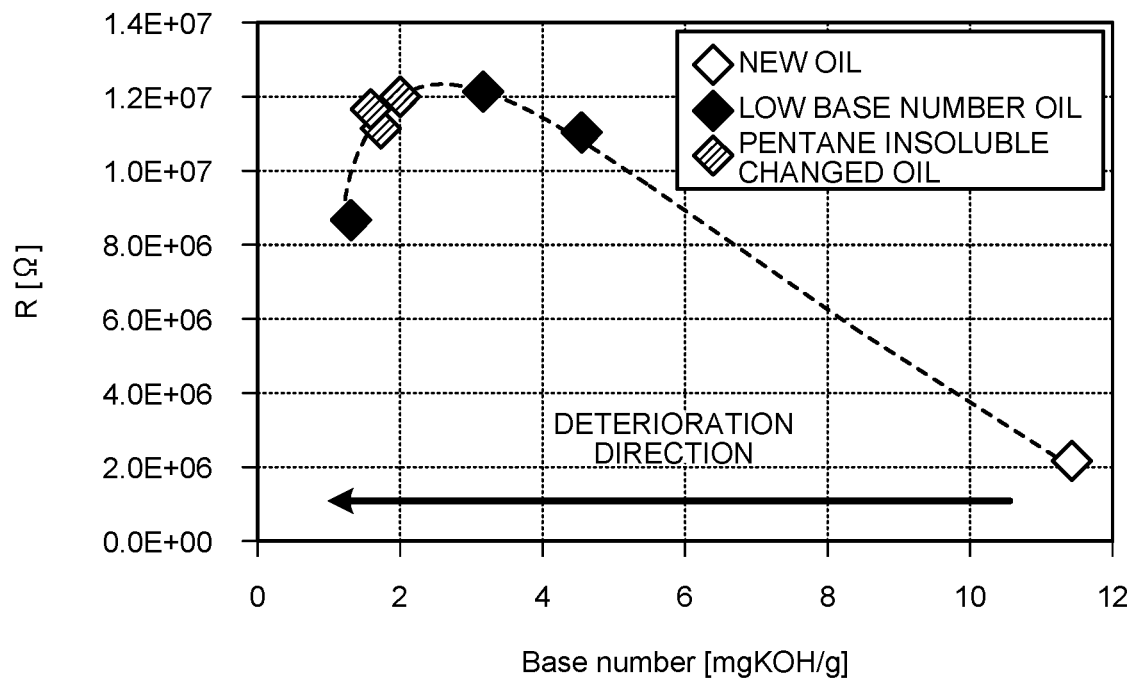
FIG. 9 is a diagram for explaining a process of detecting the base number.
Figure 10:
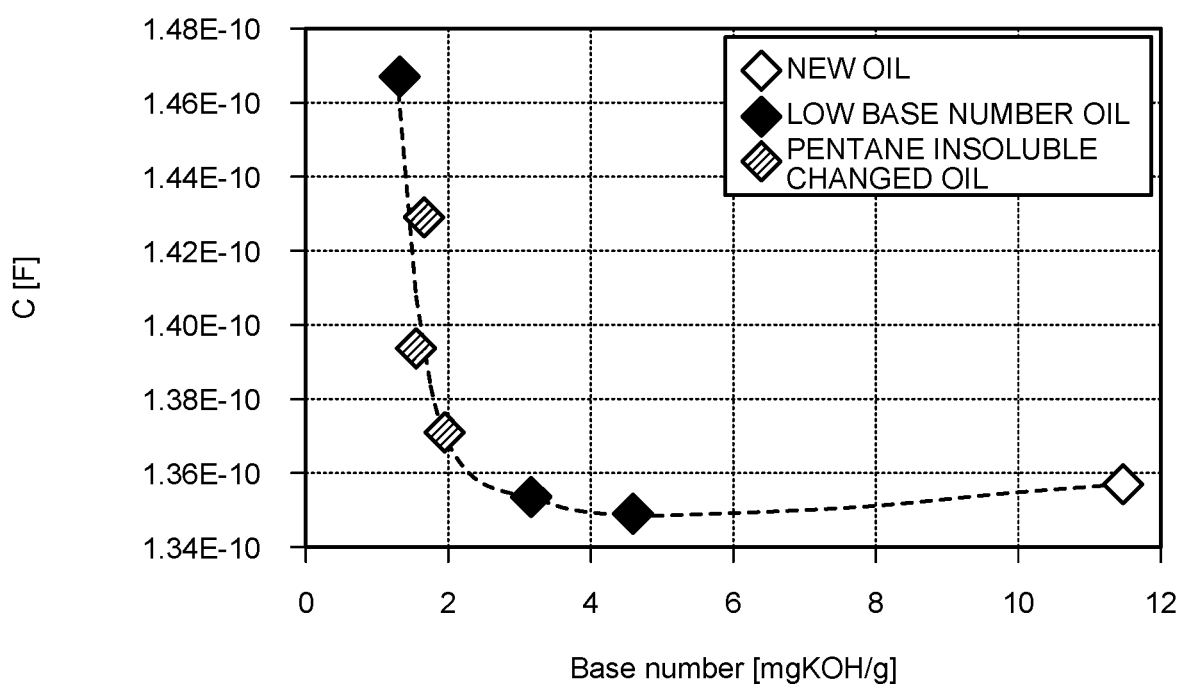
FIG. 10 is a diagram for explaining the process of detecting the base number.
Figure 11:
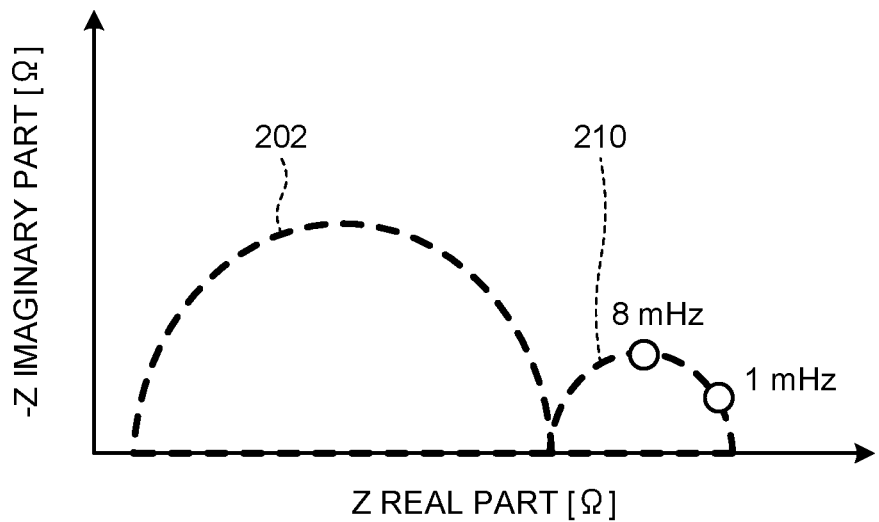
FIG. 11 is a diagram for explaining the oil deterioration detection method.
Figure 12:
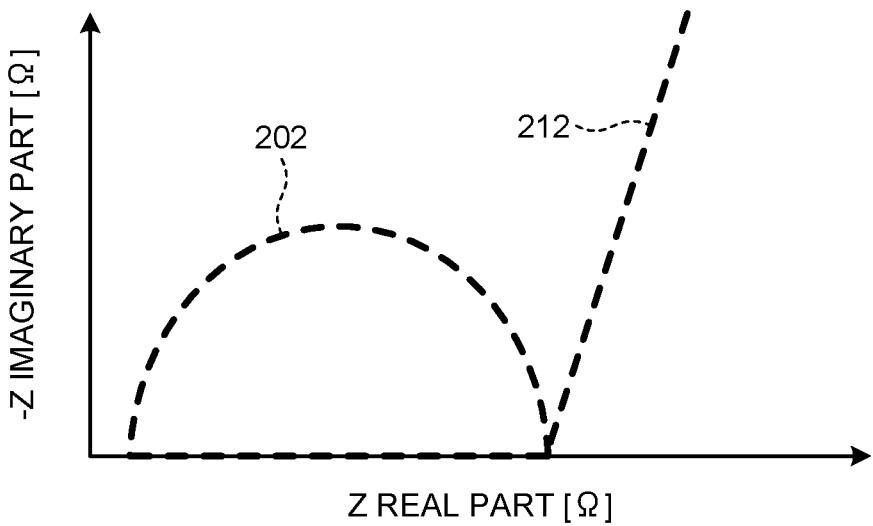
FIG. 12 is a diagram for explaining the oil deterioration detection method.
Figure 13:
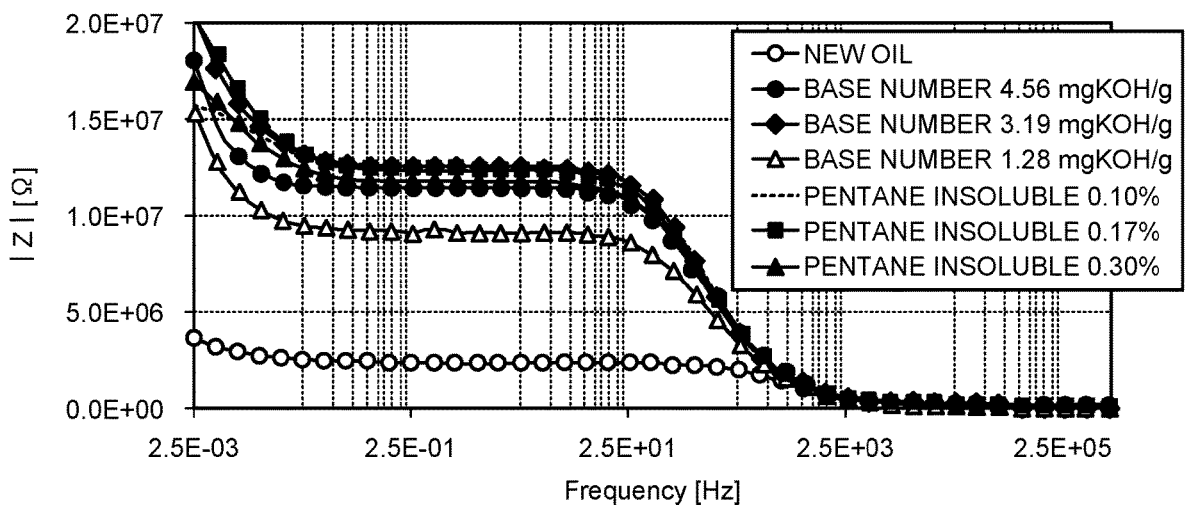
FIG. 13 is a diagram for explaining a process of detecting soot.
Figure 14:
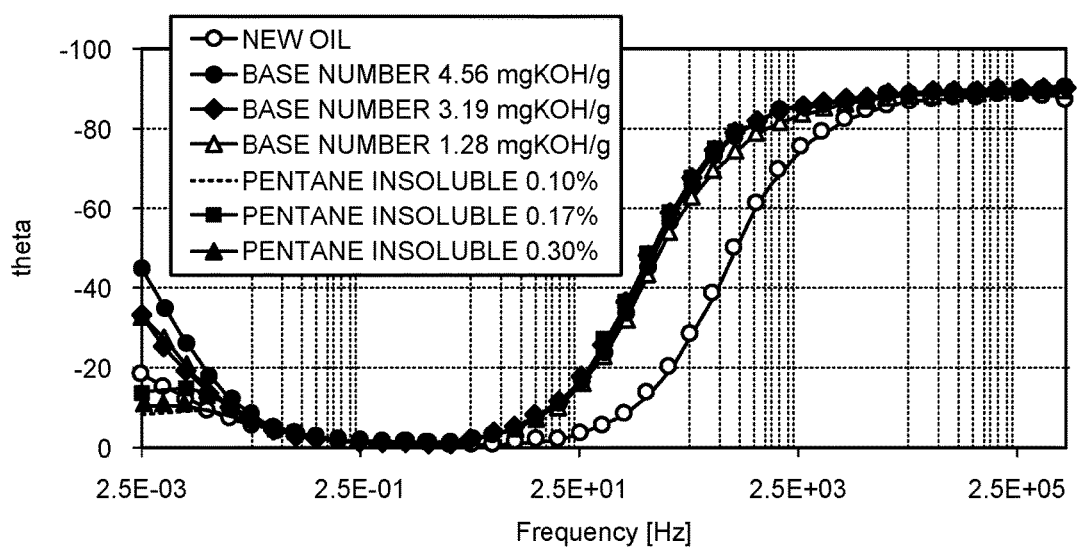
FIG. 14 is a diagram for explaining the process of detecting soot.
Figure 15:
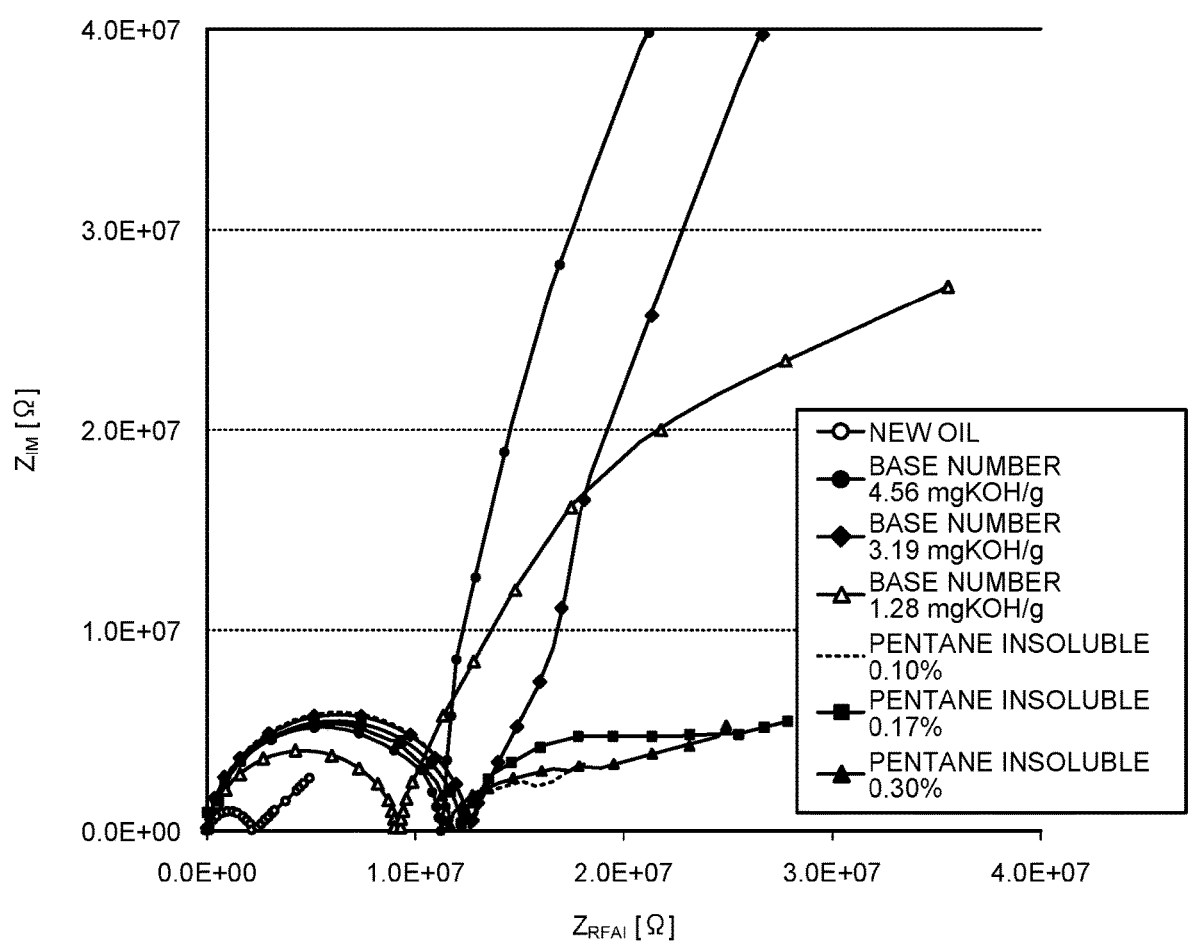
FIG. 15 is a diagram for explaining the process of detecting soot.

The following describes an example of an oil deterioration detection method performed by the oil deterioration detection system with reference to FIGS. 3 to 15. FIG. 3 is a flowchart of an example of the oil deterioration detection method performed by the oil deterioration detection system according to the present embodiment. FIG. 4 is a diagram for explaining the oil deterioration detection method. FIGS. 5 to 7 are diagrams for explaining the process of detecting the amount of moisture. FIGS. 9 and 10 are diagrams for explaining the process of detecting the base number. FIGS. 11 and 12 are diagrams for explaining the oil deterioration detection method. FIGS. 13 to 15 are diagrams for explaining the process of detecting soot.

The oil deterioration detection system 60 measures the temperature of the lubricating oil by the temperature detecting unit 103 (Step S12).

The oil deterioration detection system 60 selects the first specific frequency (Step S14). Specifically, the selector 122 selects the oscillation circuit that generates an AC voltage to be applied to the measuring unit 102. The selector 122 according to the present embodiment selects one oscillation circuit from the oscillation circuits 130, 132, and 134. The oil deterioration detection system 60 applies an AC voltage from the selected oscillation circuit to the measuring unit 102 and measures the impedance by the impedance measurement circuit 124 (Step S16).

After the impedance is measured, the oil deterioration detection system 60 determines whether all the impedances at the first specific frequencies are measured (Step S18). The oil deterioration detection system 60 according to the present embodiment uses the oscillation circuits 130, 132, and 134 and determines whether measurement of the impedances at three different first specific frequencies is completed. If the oil deterioration detection system 60 determines that the measurement is not completed (No at Step S18), it performs the processing at Step S14 again to select an oscillation circuit with which measurement is not performed and measures the impedance.

If the oil deterioration detection system 60 determines that the measurement is completed (Yes at Step S18), it performs an equivalent circuit analysis based on the results of measurement at the first specific frequencies (Step S20). FIG. 4 is a diagram for explaining the oil deterioration detection method. As illustrated in FIG. 4, the oil deterioration detection system 60 specifies three points on the Nyquist diagram based on the values of the impedance detected by the AC voltages at the three first specific frequencies and creates a first arc 202 passing through the three points. An arc 204 illustrated in FIG. 4 is a reference arc derived based on the impedance measured using the lubricating oil in the reference state. The arc 204 according to the present embodiment is an RC parallel circuit having an apex frequency of the arc of 100 Hz.

The oil deterioration detection system 60 performs a mixed moisture amount calculation process based on the results of the equivalent circuit analysis (Step S22). The oil deterioration detection system 60 performs fitting between the calculated first arc 202 and the arc 204 serving as the reference. If the oil deterioration detection system 60 determines that the first arc 202 agrees with the arc 204, it determines that no moisture is mixed in the lubricating oil. The criterion for determination is as follows: if the difference between the first arc 202 and the arc 204 serving as reference falls within a predetermined range, the oil deterioration detection system 60 can determine that the first arc 202 agrees with the arc 204. If the first arc 202 does not agree with the arc 204, the oil deterioration detection system 60 calculates the amount of moisture based on the size of the first arc 202 and the difference between the size of the first arc 202 and that of the arc 204.

FIGS. 5 to 7 are diagrams for explaining the process of detecting the amount of moisture. FIGS. 5 to 7 illustrate the results of the equivalent circuit analysis performed on the measurement results obtained by varying the amount of moisture in the same lubricating oil. FIG. 5 illustrates the relation between frequency and resistance. FIG. 6 illustrates the relation between frequency and capacitance. FIG. 7 is a Nyquist diagram created by analyzing the measurement results. As illustrated in FIGS. 5 to 7, the impedance of the lubricating oil varies with the moisture content. Specifically, as the amount of moisture increases, the arc of the Nyquist diagram becomes larger as illustrated in FIG. 7. As illustrated in FIG. 5, the relation between frequency and resistance varies with the amount of moisture. By contrast, as illustrated in FIG. 6, the capacitance serving as a C component of the equivalent circuit does not vary with changes in the amount of moisture.

Based on the relations described above, the oil deterioration detection system 60 calculates the amount of moisture contained in the lubricating oil from the first arc of the Nyquist line created based on the impedance calculated at the three first specific frequencies. FIG. 8 is a diagram for explaining the oil deterioration detection method. FIG. 8 is a graph of the relation between frequency and resistance of the lubricating oil under various conditions. As illustrated in FIG. 8, measurement is performed at three points of 1 kHz, 100 Hz, and 1 Hz as the first specific frequencies, thereby obtaining the impedances showing different characteristics of the lubricating oil.

The oil deterioration detection system 60 performs a base number calculation process based on the results of the equivalent circuit analysis (Step S26). FIGS. 9 and 10 are diagrams for explaining the process of detecting the base number. FIG. 9 is a graph of the relation between base number and resistance resulting from the equivalent circuit analysis. FIG. 10 is a graph of the relation between base number and capacitance resulting from the equivalent circuit analysis. As illustrated in FIGS. 9 and 10, the resistance component and the capacitance component of the equivalent circuit of the lubricating oil vary with the base number. The resistance increases as the base number decreases. The capacitance has small variations until the base number reaches a predetermined base number. When the base number decreases to the predetermined base number or smaller, the capacitance increases rapidly. The oil deterioration detection system 60 calculates the base number from the capacitance of the maximum value of the apex of the calculated arc and the resistance. In the present embodiment, the result of measurement at a first specific frequency of 100 Hz is a neighborhood of the maximum value of the apex of the arc. Therefore, the base number can be calculated by using the capacitance calculated using the impedance resulting from measurement at a first specific frequency of 100 Hz, the resistance, and the relation illustrated in FIGS. 9 and 10. The lubricating oil can be considered to deteriorate in performance as lubricating oil when the base number is a certain value or smaller.

Subsequently, the oil deterioration detection system 60 selects the second specific frequency (Step S28). Specifically, the selector 122 selects the oscillation circuit that generates an AC voltage to be applied to the measuring unit 102. The selector 122 according to the present embodiment selects one oscillation circuit from the oscillation circuits 136 and 138. The oil deterioration detection system 60 applies an AC voltage from the selected oscillation circuit to the measuring unit 102 and measures the impedance by the impedance measurement circuit 124 (Step S30).

After the impedance is measured, the oil deterioration detection system 60 determines whether all the impedances at the second specific frequencies are measured (Step S32). The oil deterioration detection system 60 according to the present embodiment uses the oscillation circuits 136 and 138 and determines whether measurement of the impedances at two different second specific frequencies is completed. If the oil deterioration detection system 60 determines that the measurement is not completed (No at Step S32), it performs the processing at Step S28 again to select an oscillation circuit with which measurement is not performed and measures the impedance.

If the oil deterioration detection system 60 determines that the measurement is completed (Yes at Step S32), it performs an equivalent circuit analysis based on the results of measurement at the second specific frequencies (Step S34). FIGS. 11 and 12 are diagrams for explaining the oil deterioration detection method. As illustrated in FIGS. 11 and 12, the oil deterioration detection system 60 specifies three points on a Nyquist diagram based on the values of the impedance detected at the AC voltages at the two second specific frequencies and on the maximum value of the real axis of the first arc 202 (the point at which the imaginary number is zero) and creates second arcs 210 and 212 passing through the three points. FIG. 11 illustrates the second arc 210 calculated based on the lubricating oil containing impurities. FIG. 12 illustrates the second arc 212 calculated based on the lubricating oil containing no impurities. The foreign matter according to the present embodiment is soot. As illustrated in FIGS. 11 and 12, if no soot is mixed, the diameter of the second arc 212 increases, and the second arc 212 can be approximated to a straight line on the scale of the first arc 202.

The oil deterioration detection system 60 performs a mixed foreign matter amount calculation process based on the results of the equivalent circuit analysis (Step S36). The oil deterioration detection system 60 performs fitting between the calculated second arc and the second arc serving as the reference. If the oil deterioration detection system 60 determines that the second arc agrees with the reference second arc, it determines that soot is mixed in the lubricating oil. The criterion for determination is as follows: if the difference between the calculated second arc and the reference second arc falls within a predetermined range, the oil deterioration detection system 60 can determine that the calculated second arc agrees with the reference second arc. If the calculated second arc agrees with the reference second arc, the oil deterioration detection system 60 calculates the amount of soot based on the size of the second arc and the inclination of the second arc when linearly approximated to a predetermined value on the real axis. If the second arc is divergent or if the second arc is larger than a predetermined size, the oil deterioration detection system 60 may determine that no soot is contained.

FIGS. 13 to 15 are diagrams for explaining the process of detecting soot. FIGS. 13 to 15 illustrate the results of the equivalent circuit analysis performed on the measurement results obtained by varying the component of impurities in the same lubricating oil. FIG. 13 illustrates the relation between frequency and resistance. FIG. 14 illustrates the relation between frequency and capacitance. FIG. 15 is a Nyquist diagram created by analyzing the measurement results. As illustrated in FIGS. 13 to 15, the impedance of the lubricating oil at the frequencies varies with changes in the component of impurities. As illustrated in FIG. 15, if no soot is contained, the diameter of the second arc increases, and the second arc is substantially divergent; and if soot is contained, the second arc can form an approximate line with approximately the same height as that of the first arc. The oil deterioration detection system 60 according to the present embodiment calculates the amount of soot based on the impedance at an AC voltage of 0.008 Hz.

The oil deterioration detection system 60 according to the present disclosure can detect deterioration of the lubricating oil due to moisture, base number (acid), and foreign matter (soot) by detecting the impedance of the lubricating oil at the first specific frequencies and the second specific frequencies and performing the equivalent circuit analysis. Specifically, the oil deterioration detection system 60 can evaluate the moisture and the base number by detecting the impedance at three or more first specific frequencies in the first frequency range and performing evaluation using the Nyquist diagram. In addition, the oil deterioration detection system 60 can evaluate the soot by detecting the impedance at two or more second specific frequencies in the second frequency range and performing evaluation using the Nyquist diagram. Therefore, the oil deterioration detection system 60 can suitably detect moisture, foreign matter, and corrosive component (base number) that may possibly have harmful effects on the sliding parts when the lubricating oil is supplied to the sliding parts.

While the oil deterioration detection system 60 according to the embodiment described above detects the amount of moisture, the base number, and the soot as the deterioration state of the lubricating oil, it may detect only the amount of moisture and the base number or only the amount of moisture. FIG. 16 is a schematic of a schematic configuration of the oil deterioration detection system according to the present embodiment. In an oil deterioration detection system 60a illustrated in FIG. 16, a frequency control unit 121a includes the oscillation circuits 130, 132, and 134 and does not include the oscillation circuits 136 and 138. The oil deterioration detection system 60a includes the oscillation circuits that generate an AC voltage in the first frequency range alone and does not include the oscillation circuits that generates an AC voltage in the second frequency range. With this configuration, the oil deterioration detection system 60a can detect the deterioration state of the lubricating oil with fewer oscillation circuits although the amount of information on the detectable deterioration state is reduced.

While the number of first specific frequencies in the first frequency range according to the present embodiment is three, it simply needs to be three or more and may be four or five or more. While the number of second specific frequencies in the second frequency range according to the present embodiment is two, it simply needs to be two or more and may be three or four or more.

The oil deterioration detection system 60, 70, and 80 according to the present disclosure each includes the measurement device 100 and the arithmetic processing device 101. The measurement device 100 measures an impedance by applying an AC voltage at at least three first specific frequencies selected from a first frequency range to counter electrodes when oil to be evaluated passes between the counter electrodes. The arithmetic processing device 101 performs an analysis based on the impedances at at least three first specific frequencies measured by the measurement device to calculate an arc of impedance on a Nyquist diagram, and when the calculated arc is larger than a reference arc calculated in advance of the oil to be evaluated by a predetermined value or larger, determines that moisture is mixed and calculates the amount of moisture based on the shape of the calculated arc. The arithmetic processing device (oil deterioration detection device) 101 performs an analysis based on impedances at at least three first specific frequencies selected from a first frequency range to calculate an arc of impedance on a Nyquist diagram, the impedances being measured by applying an AC voltage at the at least three first specific frequencies to counter electrodes when oil to be evaluated passes between the counter electrodes, and when the calculated arc is larger than a reference arc calculated in advance of the oil to be evaluated by a predetermined value or larger, determines that moisture is mixed and calculates the amount of moisture based on the shape of the calculated arc.

Thus, the arithmetic processing device can detect the amount of moisture that causes deterioration of oil by detecting the impedance.

The first frequency range is preferably 50 mHz to 7 MHz. The arithmetic processing device can suitably detect the amount of moisture and the base number by setting the first frequency range to the range described above.

The first specific frequencies preferably include a frequency of 50 mHz to 10 Hz, a frequency of 10 Hz to 500 Hz, and a frequency of 500 Hz to 7 MHz. The arithmetic processing device can calculate the arc of impedance on the Nyquist diagram with high accuracy by including three frequencies satisfying the ranges described above as the first specific frequencies.

The measurement device preferably includes a plurality of oscillation circuits that output the respective first specific frequencies and a selector that switches the oscillation circuits. Thus, the measurement device can switch the frequencies with a simpler configuration. The measurement device may switch or change the frequencies of the AC voltage by another mechanism.

The arithmetic processing device preferably calculates a resistance by considering capacitance of the calculated arc to be the same value as capacitance of the reference arc and calculates the amount of moisture. Thus, the arithmetic processing device can suitably calculate the amount of moisture.

The arithmetic processing device preferably calculates a base number from capacitance of the maximum value of the apex of the calculated arc and the resistance. Thus, the arithmetic processing device can suitably detect the base number.

The measurement device preferably measures impedances by applying an AC voltage at at least two second specific frequencies selected from a second frequency range lower than the first frequency range to the counter electrodes. The arithmetic processing device preferably performs an analysis based on the maximum value of the real axis of a first arc of impedance serving as the arc of impedance based on the first specific frequencies and on the impedance at the at least two second specific frequencies measured by the measurement device, to calculate a second arc of impedance on a Nyquist diagram, and determines whether an impurity is mixed by comparing the second arc with a reference arc calculated in advance of the oil to be evaluated. Thus, the arithmetic processing device can suitably detect foreign matter.

The second frequency range is preferably 0.25 mHz to 50 mHz. Thus, the arithmetic processing device can suitably detect foreign matter.

The impurity is preferably soot. The arithmetic processing device can suitably detect inclusion of soot.

The oil deterioration detection method according to the present disclosure includes: measuring impedances by applying an AC voltage at at least three first specific frequencies selected from a first frequency range to counter electrodes when oil to be evaluated passes between the counter electrodes; performing an analysis based on the impedances at the at least three first specific frequencies measured by the measurement device to calculate an arc of impedance on a Nyquist diagram; and when the calculated arc is larger than a reference arc calculated in advance of the oil to be evaluated by a predetermined value or larger, determining that moisture is mixed and calculating the amount of moisture based on the shape of the calculated arc. Thus, the oil deterioration detection system 60 can detect the amount of moisture that causes deterioration of oil by detecting the impedance.

The oil deterioration detection method preferably further includes calculating a base number from capacitance of the maximum value of the apex of the calculated arc and a resistance. Thus, the oil deterioration detection system 60 can detect the base number that causes deterioration of oil by detecting the impedance.

The oil deterioration detection method preferably includes: measuring impedances by applying an AC voltage at at least two second specific frequencies selected from a second frequency range lower than the first frequency range to the counter electrodes; performing an analysis based on the maximum value of the real axis of a first arc of impedance serving as the arc of impedance based on the first specific frequencies and on the measured impedances at the at least two second specific frequencies and calculating a second arc of impedance on a Nyquist diagram; and determining whether an impurity is mixed by comparing the second arc with a reference arc calculated in advance of the oil to be evaluated. Thus, the oil deterioration detection system 60 can detect inclusion of foreign matter that causes deterioration of oil by detecting the impedance.

REFERENCE SIGNS LIST

10 Power generation system
12 Engine body
14 Supercharger
16 Generator
18 Lubricating oil supply unit
20 Lubricating oil tank
22 Lubricating oil line
24 Pump
26 Cooler
28 Filter
30 Backwash strainer
32 Bypass piping
34 Three-way valve
50 First sensor unit
52 Second sensor unit
54 Third sensor unit
60, 70, 80 Oil deterioration detection system
62, 72, 82 Sensor line
64, 76, 84 Valve
100 Measurement device
101 Arithmetic processing device (lubricating oil deterioration detection device)
102 Measuring unit
104 Substrate
106 Power source
110 Flow path
112 Counter electrode
114 Action electrode
120 Power supply circuit
121 Frequency control unit
122 Selector
124 Impedance measurement circuit
126 Arithmetic unit
128 Communication unit
130, 132, 134 Oscillation circuit
140 CPU
142 Memory

The invention claimed is:

1. An oil deterioration detection device comprising a processor configured to:
perform an analysis based on impedances at at least three first specific frequencies selected from a first frequency range to calculate an arc of impedance on a Nyquist diagram, the impedances being measured by applying an AC voltage at the at least three first specific frequencies to counter electrodes when oil to be evaluated passes between the counter electrodes, and
when the calculated arc is larger than a reference arc calculated in advance of the oil to be evaluated by a predetermined value or larger, determine that moisture is mixed and calculate an amount of moisture based on a shape of the calculated arc,
wherein the oil deterioration detection device configured to obtain impedances measured by applying an AC voltage at at least two second specific frequencies selected from a second frequency range lower than the first frequency range to the counter electrodes, perform an analysis based on a maximum value of a real axis of a first arc of impedance serving as the arc of impedance based on the first specific frequencies and on the measured impedances at the at least two second specific frequencies, to calculate a second arc of impedance on a Nyquist diagram, and determine whether an impurity is mixed by comparing the second arc with a reference arc calculated in advance of the oil to be evaluated.

2. The oil deterioration detection device according to claim 1, wherein the first frequency range is 50 mHz to 7 MHz.

3. The oil deterioration detection device according to claim 1, wherein the first specific frequencies include a frequency of 50 mHz to 10 Hz, a frequency of 10 Hz to 500 Hz, and a frequency of 500 Hz to 7 MHz.

4. The oil deterioration detection device according to claim 1, wherein the oil deterioration detection device is configured to calculate a resistance by considering capacitance of the calculated arc to be a same value as capacitance of the reference arc and calculates the amount of moisture.

5. The oil deterioration detection device according to claim 1, wherein the oil deterioration detection device is configured to calculate a base number from capacitance of a maximum value of an apex of the calculated arc and the resistance.

6. The oil deterioration detection device according to claim 1, wherein the second frequency range is 0.25 mHz to 50 mHz.

7. The oil deterioration detection device according to claim 1, wherein the impurity is soot.

8. An oil deterioration detection system comprising:
a measurement device configured to measure impedances by applying an AC voltage at at least three first specific frequencies selected from a first frequency range to counter electrodes when oil to be evaluated passes between the counter electrodes; and the oil deterioration detection device according to claim 1, wherein the measurement device comprises:
- a plurality of oscillation circuits configured to output the respective first specific frequencies; and
- a selector configured to switch the oscillation circuits.

9. An oil deterioration detection method comprising:

measuring impedances by applying an AC voltage at at least three first specific frequencies selected from a first frequency range to counter electrodes when oil to be evaluated passes between the counter electrodes;

performing an analysis based on the measured impedances at the at least three first specific frequencies to calculate an arc of impedance on a Nyquist diagram;

when the calculated arc is larger than a reference arc calculated in advance of the oil to be evaluated by a predetermined value or larger, determining that moisture is mixed and calculating an amount of moisture based on the shape of the calculated arc, measuring impedances by applying an AC voltage at least two second specific frequencies selected from a second frequency range lower than the first frequency range to the counter electrodes;

performing an analysis based on a maximum value of a real axis of a first arc of impedance serving as the arc of impedance based on the first specific frequencies and on the measured impedances at the at least two second specific frequencies and calculating a second arc of impedance on a Nyquist diagram; and determining whether an impurity is mixed by comparing the second arc with a reference arc calculated in advance of the oil to be evaluated.

10. The oil deterioration detection method according to claim 9, further comprising calculating a base number from capacitance of a maximum value of an apex of the calculated arc and a resistance.

* * * * *